(12) United States Patent
Weinkauf

(10) Patent No.: US 11,337,789 B2
(45) Date of Patent: May 24, 2022

(54) INFERIOR VENA CAVA (IVC) FILTER AND RELATED METHODS

(71) Applicant: ARIZONA BOARD OF REGENTS ON BEHALF OF THE UNIVERSITY OF ARIZONA, Tucson, AZ (US)

(72) Inventor: Craig C. Weinkauf, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 17 days.

(21) Appl. No.: 16/626,124

(22) PCT Filed: Jun. 28, 2018

(86) PCT No.: PCT/US2018/039942
§ 371 (c)(1),
(2) Date: Dec. 23, 2019

(87) PCT Pub. No.: WO2019/006086
PCT Pub. Date: Jan. 3, 2019

(65) Prior Publication Data
US 2020/0222169 A1    Jul. 16, 2020

Related U.S. Application Data

(60) Provisional application No. 62/525,936, filed on Jun. 28, 2017.

(51) Int. Cl.
*A61F 2/01* (2006.01)

(52) U.S. Cl.
CPC .............. *A61F 2/0105* (2020.05); *A61F 2/011* (2020.05); *A61F 2002/016* (2013.01); *A61F 2210/0014* (2013.01); *A61F 2230/0067* (2013.01)

(58) Field of Classification Search
CPC ........ A61F 2002/016; A61F 2210/0014; A61F 2230/0067; A61F 2/01; A61F 2002/011; A61F 2/011; A61F 2230/008; A61F 2230/005; A61F 2230/0093; A61F 2230/0008; A61F 2230/0091; A61F 2/0108; A61F 2/012; A61B 17/221; A61B 2017/2215; A61B 2017/22034; A61B 2017/2212; A61B 2017/00623; A61B 2017/00778; A61B 17/12022; A61B 2017/00615; A61B 2017/2217; A61M 29/00; A61M 2025/0096; A61M 2210/12
USPC .......................... 606/200; 128/830, 831, 833
See application file for complete search history.

(56) References Cited

U.S. PATENT DOCUMENTS

| | | | |
|---|---|---|---|
| 5,836,968 A | * | 11/1998 | Simon ....................... A61F 2/01 606/200 |
| 6,251,122 B1 | | 6/2001 | Tsukernik |
| 8,029,529 B1 | | 10/2011 | Chanduszko |
| 9,308,073 B2 | | 4/2016 | Fischer et al. |

(Continued)

*Primary Examiner* — Kelly J Bekker
*Assistant Examiner* — Andrew P. Restaino
(74) *Attorney, Agent, or Firm* — Nguyen Tarbet LLC

(57) ABSTRACT

The present disclosure is directed to an Inferior Vena Cava (IVC) filter apparatus and related methods. The IVC filter apparatus comprises a body having a proximal hook thereon. A plurality of filter legs extends away from the proximal hook. A distal hook is position interior to at least a portion of the plurality of legs.

15 Claims, 2 Drawing Sheets

(56) References Cited

U.S. PATENT DOCUMENTS

| | | | |
|---|---|---|---|
| 2008/0275491 A1* | 11/2008 | Niermann | A61F 2/01 606/200 |
| 2009/0299404 A1* | 12/2009 | Chanduszko | A61F 2/01 606/200 |
| 2012/0089173 A1 | 4/2012 | Tekulve | |
| 2013/0267848 A1 | 10/2013 | Fearnot et al. | |
| 2015/0265390 A1 | 9/2015 | Klausen | |

\* cited by examiner

INFERIOR VENA CAVA (IVC) FILTER AND RELATED METHODS

CROSS REFERENCE

This application claims priority to U.S. Provisional Patent Application No. 62/525,936, filed Jun. 28, 2017, the specifications of which are incorporated herein in their entirety by reference.

FIELD OF THE INVENTION

The present invention relates to medical devices for the human circulatory system and more particularly is related to Inferior Vena Cava filters and related methods.

BACKGROUND OF THE INVENTION

As is well known to those skilled in the art, the heart pumps blood into the lungs via the pulmonary arteries. Blood is oxygenated in the lungs and returns to the heart. The blood is then pumped out to the rest of the body through the aorta. The blood then returns via many veins that drain into the Inferior Vena Cava (IVC), which carries blood to the right side, or atrium, of the heart. The IVC is the largest vein in the human body, and thus, acts as the principle pathway for blood to move from the lower and middle body back to the heart.

Blood clots (thrombi) are formed throughout the human body by a clumping of the blood from a liquid to a gel-like or semisolid state. While blood clots are healthy for the human body when they stop bleeding, they are also prone to causing complications within the circulatory system. Blood clots can form in veins for various reasons, including infection, sedentary lifestyle, obstruction, surgery, hormonal imbalance, or other reasons. Sometimes these blood clots are large, and they form in the veins within the legs, such as the femoral vein, which are some of the largest in the human body. This condition is known as Deep Vein Thrombosis (DVT). Certain conditions, unknown and known, can cause blood clots or other emboli to break loose from a location within the vein, travel through the IVC, and into the right side of the heart. They then get pumped into the lungs where they get stuck in a blood vessel and cause it to become clogged, thus preventing blood flow. This condition is called a Pulmonary Embolism (PE). Since PE blocks blood from getting to the lungs, it is often fatal.

In patients with high risk for PE, it is possible to place a small filter in the IVC which can trap the blood clot at the filter's location before the blood clot reaches the heart or lungs and causes serious complications. This filter is known as an IVC filter. The IVC filter is a device formed from metal or other suitable materials which is inserted into a patient's IVC in a collapsed configuration and then is moved to an expanded configuration once in the desired position. In the expanded configuration, the IVC filter has a basket area which allows blood to flow through, but is sized to capture a blood clot that is moving with the blood flow. Some IVC filters have a hook, which facilitates insertion and removal of the IVC filter, and multiple legs or netting that form the basket area.

While IVC filters are successful in preventing blood clots from reaching the heart and lungs, they can cause other medical complications. For example, the IVC filters can cause IVC thrombosis, which can occur due to the IVC filter being a foreign object within the vein, causing thrombosis (clotting) of the IVC and eventually leading to a total blockage of the IVC. As shown, a clot has formed at the location of the IVC filter, which is preventing blood flow from the lower portion of the IVC. IVC thrombosis causes severe disability in some patients. If the IVC is blocked, blood has difficulty draining out of tissues in the lower body and back to the heart. This can cause severe leg swelling, pain, blisters and wounds. It can prevent people from walking and can cause them to become disabled.

Additionally, conventional IVC filters are associated with other complications and risks. For example, IVC filters are also known to break and send shards of metal through the bloodstream. These traveling shards of metal can pierce other organs and cause irreversible damage. Due to the small size of the pieces of the IVC filter, doctors are often unable to safely remove the metal shards from the patient. Another complication is that the IVC filters can move from their original and intended placement to another part of the body, which can cause damage to the unintended location or the portion of the IVC through which the IVC filter moves in the expanded configuration. Some of the movement IVC filters experience is not translational movement along the IVC, but rather, is angular and/or lateral movement (e.g., axial tilting), where the hook portion of the IVC filter contacts the internal vein wall of the IVC. This positioning of the IVC filter can significantly decrease the ability to remove the IVC filter without complications, and in some cases, it can prevent removal of the IVC filter entirely. To prevent complications, IVC filters need to be retrieved from the patient as soon as possible. However, in 20% to 50% of cases, IVC filters are not removed or cannot be retrieved from the IVC.

Proper IVC filter removal from a patient is as follows. When an IVC filter is positioned correctly within the IVC, a doctor is able to place a snare within the IVC and make contact with the IVC filter hook from above with deployable snare loop on the end thereof. Once the IVC filter is appropriately snared at the hook, a sheath is slid over the snare loop and the hook to a point where the sheath contacts the legs of the IVC filter, causing them to collapse inwards towards each other. Then, the IVC filter, with the sheath in a covered position, is removed from the IVC by the doctor pulling the snare from the patient's body.

While there are some medical indications for IVC filters to be left in place for life of the patient, and sometimes patients or doctors forget to take them out, more often than not failure to retrieve the IVC filter is due to the possibility of complications with removal. For example, if the IVC filter is positioned incorrectly during placement or becomes tilted at some later point, the IVC filter is not removed or cannot be removed because the hook portion of the IVC filter, i.e., the tip of the IVC filter, is embedded in the IVC wall and cannot be removed. Often, tilt of the IVC filter occurs during the initial deployment. When the filter tilts, the hook end of the IVC filter may become embedded within the sidewall of the IVC. When tilting occurs, it's difficult to remove the hook from the IVC wall. However, leaving the IVC filter in place while tilted makes the problem worse because tissue grows around the hook.

U.S. Pat. No. 8,023,529 describes a vessel filter having two sliding members at opposite ends of the filter, each member having a recovery member. Each sliding member slides over a cone formed by a plurality of struts and collapses the cone by compressing the struts. U.S. Pat. No. 9,308,073 describes a filter having both a fixed and a movable hub with two coupling members extending from the two hubs in opposite directions. The hub slides between two positions and compresses a plurality of struts to collapse the filter. Both of these filters have sliding parts which may be prone to breakage and may cause metals shards to enter the bloodstream. Additionally, both filters have wider bodies to allow for the sliding parts. The thickness of these filter bodies may cause a reduction or impedance of blood flow.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide an IFC filter apparatus having two fixed hooks fixed at opposite ends of a body and a plurality of fixedly attached legs projecting radially from the body. Without wishing to limit the invention to any particular theory or mechanism, it is believed that the fixed attachment of the hooks and legs will provide for a strong apparatus which will not break and send shards of metal through the bloodstream.

In preferred embodiments of the present invention, the filter apparatus has a ratio between a length of a proximal segment of the body and a total length of the apparatus of less than about 1:5. This proximal segment includes a proximal hook which is configured to be used for removal of the filter apparatus. Without wishing to limit the present invention to a particular theory or mechanism, it is believed that this ratio gives the proximal hook a low potential to imbed into the wall of the IVC if the apparatus tilts. Without wishing to limit the present invention to a particular theory or mechanism, if the apparatus does tilt and the proximal hook does embed into the wall of the IVC, a distal hook opposite from the proximal hook will allow for easy repositioning of the filter apparatus and a freeing of the proximal hook from the wall of the IVC. In preferred embodiments, the distal hook is shorter than the filter legs but long enough to be easily engaged by a snare.

One of the unique and inventive technical features of the present invention is that the apparatus comprises a body with fixed hooks at opposite ends which has a cross sectional area of less than 5 mm$^2$. This small cross-sectional area is made possible by having the components of the filter apparatus fixedly attached. Without wishing to limit the invention to any theory or mechanism, it is believed that the technical feature of the present invention advantageously provides for better positioning and easier removal of the device while providing for uninhibited blood flow through the filter apparatus. The smaller the cross-sectional area of the device, the less the device will inhibit blood flow. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 1A:
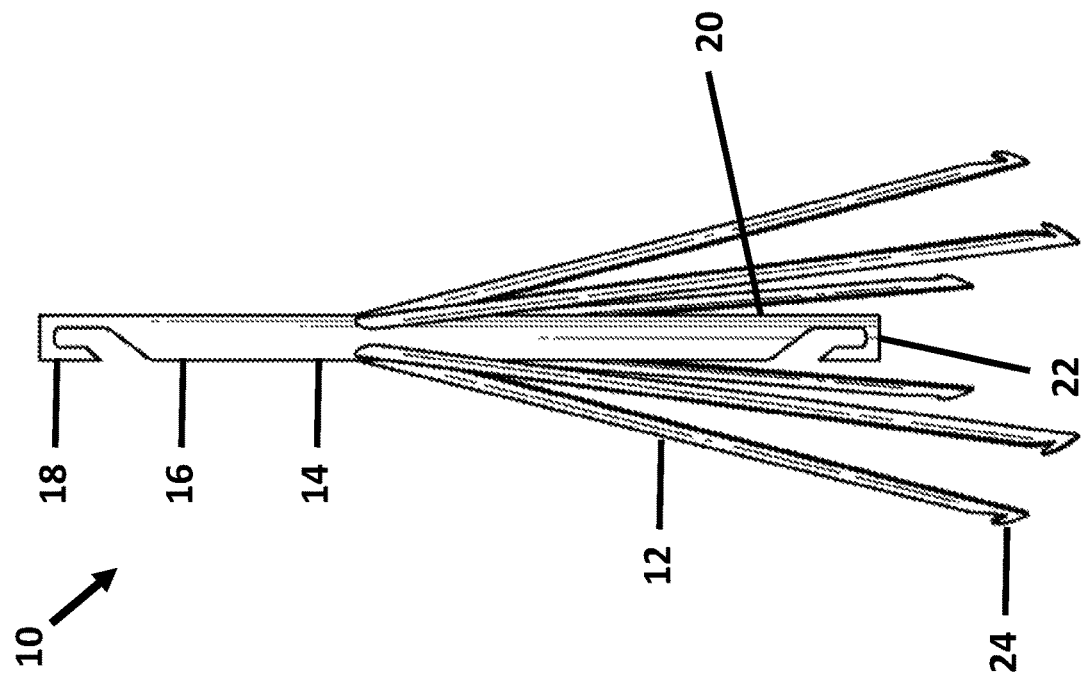
FIG. 1A shows an illustration of an IVC filter of the present invention, having legs in an expanded position.
Figure 1B:
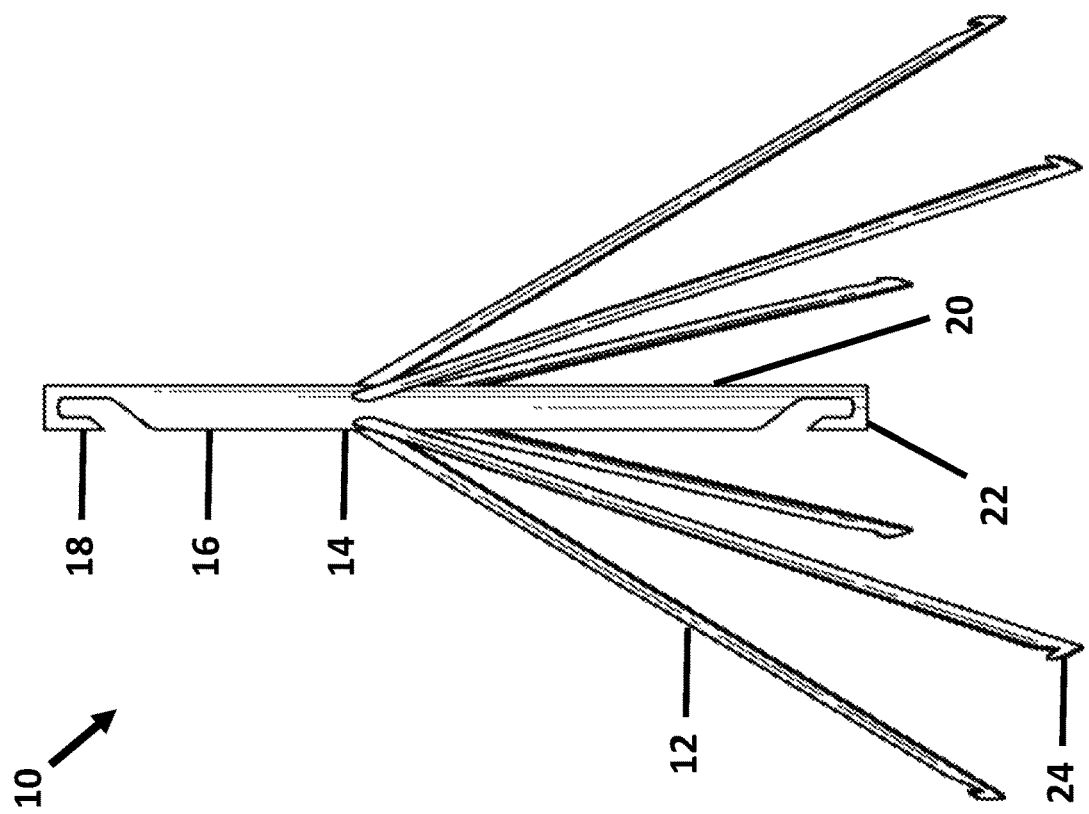
FIG. 1B shows an illustration of an IVC filter of the present invention, having legs in a collapsed position.
Figure 2B:
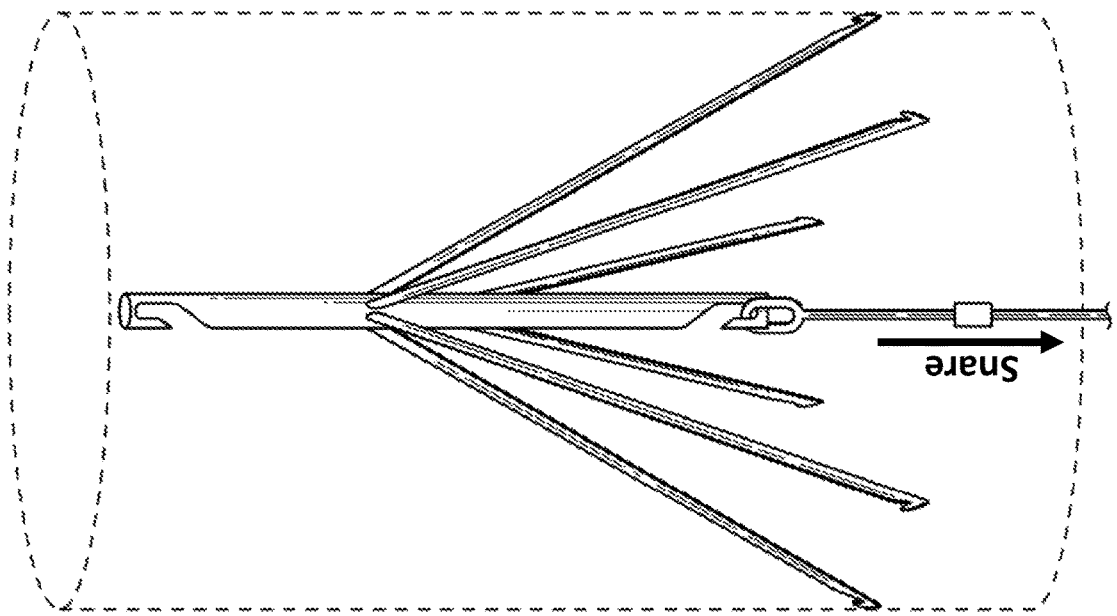
FIG. 2B shows illustration of an IVC filter of the present invention, with a snare loop engaging with the distal loop for positioning or removal.
Figure 2A:
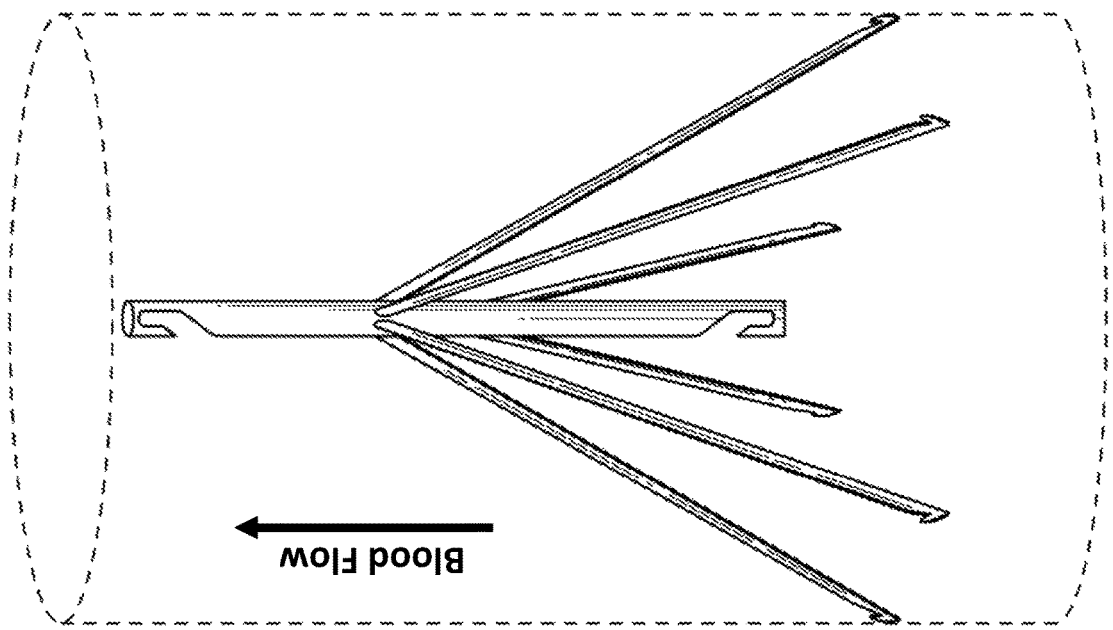
FIG. 2A shows an illustration of an IVC filter of the present invention, inserted within an IVC vein.

As can be understood from the Background, there are numerous shortcomings of conventional IVC filters. Maldeployment occurs too frequently, which causes tilting and increases the probability of the IVC filter hook embedding into the IVC wall. Once the hook is positioned near the wall, contacting the wall, or embedded within the wall, there is no ability to pull the hook back away from the wall. Additionally, conventional IVC filters with multiple components soldered together can break and the small legs can embed in tissue or migrate.

To overcome these problems, an improved IVC filter is disclosed. As shown, the IVC filter (10) includes a plurality of legs (12) which are connected to a body (14). The body (14) includes a proximal segment (16) for a proximal hook (18) on the top of the IVC filter (10). The presence of the proximal segment (16) and proximal hook (18) at the top of the IVC filter (10) may not be dissimilar from that of a conventional IVC filter, however, the dimensions of the components are modified from those of a conventional IVC filter to increase performance and decrease complications.

The IVC filter (10) includes a distal segment (20) with a distal hook (22) thereon. The distal segment (20) is positioned opposite the proximal segment (16) and proximal hook (18) on the body (14), such that the distal segment (20) is located substantially between the legs (12). The distal segment (20) may be positioned along an axis of the IVC filter (10), such that it is roughly centered between all of the legs (12), of which the number may vary, but commonly six legs (12) may be used. The length of the distal segment (20) may vary by design, but in one example, the length may allow for placement of the distal hook (22) approximately half that of the length of the legs (12). The legs (12) may be formed from a durable, movable material such that they can be expanded outwards during use of the IVC filter (10). Tines (24) may be formed at the terminating end of each of the legs (12).

Overall, the IVC filter (10) may have a similar basic shape to that of a conventional premium IVC filter (e.g., OPTEASE® IVC Filter), in that, the IVC filter (10) has a proximal hook (18) on a proximal segment (16) on one side thereof and six legs (12) with short tines (24) on the opposing side. Some of the improvements of the IVC filter (10) over a conventional IVC filter, include the shorter proximal segment (16) on the IVC filter (10) and the presence of the distal segment (20) with the distal hook (22). These new features allow the doctor using the IVC filter (10) to better control the placement, deployment, and retrieval of the IVC filter (10) within the patient, thereby providing optimal use and decreased risk of the IVC filter (10).

It has been found that decreasing the length of the proximal segment (16) as compared to conventional devices allows the proximal hook (18) all to be located closer to the filter body (14). In conventional devices, the length of the proximal segment is greater than %16" (0.5625 inch, 14.29 mm), as measured from the connection points of the legs to the body. In the IVC filter (10), the length of the proximal segment (16) is approximately 7⁄16" (0.4375 inch, 11.11 mm), as measured from the terminating end of the proximal hook (18) to the connection points of the legs (12) to the body (14). This change allows the IVC filter (10) to have a lower potential to embed the proximal hook (18) into the sidewall of IVC during initial deployment of the IVC filter (10) if tilting occurs. If the body of the IVC filter (10) starts to tilt, the proximal hook (18) will be moved closer to the sidewall of the IVC, but it will need to tilt to a greater degree than a comparable conventional IVC filter in order to make contact with the inner sidewall of the IVC. Thus, the IVC filter (10) will be able to sustain tilting to a greater degree than a conventional device without the proximal hook (18) contacting the IVC. Additionally, the greater the tilt angle required for the IVC filter (10) to make contact with the IVC means that the doctor deploying the IVC will have a greater opportunity to correct the position of the IVC and prevent contact between the proximal hook (18) and the IVC.

With regards to the distal segment (20) and the distal hook (22) thereon, these components are designed to be long so that it is easy to snare after IVC filter (10) is deployed, which may be needed if the IVC filter (10) does not deploy correctly upon insertion. Commonly, the IVC filter (10) is placed within the patient's IVC from his or her groin area, where the IVC filter (10) is housed within a sheath until it reaches the intended position within the IVC, at which point it is expelled from the sheath and deployed into the IVC. If poor deployment occurs, e.g., if there is tilting or another complication, the doctor will have the ability to access the IVC filter (10) via the IVC from the groin access point, where he or she can snare the distal hook (22) on the distal segment (20) and pull the proximal hook (18) away from the wall of the IVC. The use of the distal hook (22) will make removal or reorientation of a tilted IVC filter (10) much easier than conventional IVC filters because the proximal hook (18) can be repositioned before it embeds and fibroses into IVC wall.

Retrieval of IVC filters commonly occurs from a location above the position of the IVC filter, such as the jugular vein. The doctor snares the hook of the IVC filter from above, collapses the legs of the IVC filter with a sheath, and then removes the device. However, if complications exist during retrieval of the IVC filter (10) using this conventional methodology with the proximal hook (18), the doctor will be able to use a second snare from a location below the IVC filter (10) to contact the distal hook (22) on the distal segment (20) and re-position the IVC filter (10) or gain additional leverage to assist with removal. For example, the distal hook (22) allows for immediate straightening of the IVC filter (10) if it is tilted after initial deployment, and also for additional access to move the IVC filter (10) if it is tilted when trying to remove the IVC filter (10) at a later point. The ability to manipulate the position of the IVC filter (10) from either an above position or a below position, or in some situations both above and below positions concurrently using two snares, allows the doctor to better prevent harmful complications normally associated with conventional IVC filters. In turn, preventing complications improves patient safety and the patient's experience, it can lower medical costs of procedures, and it can increase the availability of the IVC filter (10) for otherwise high-risk patients.

The exact specifications of the novel IVC filter (10) disclosed herein may vary depending on design. However, it may be preferable for the IVC filter (10) to have a distal segment (20) and distal hook (22) that are slender, e.g., equal to or less than ⅛" (0.125 inch) to impede blood flow minimally, so the thrombosis rate does not exceed that of conventional IVC filters. The IVC filter (10) may be manufactured from various materials used within the medical profession, such as Nitinol. The IVC filter (10) may include various manufacturing or construction processes, including construction of the IVC filter (10) in two pieces, with the main body (14), the proximal segment (16), the proximal hook (18), and the legs (12) cut from one piece of material, and the distal segment (20) and the distal hook (22) formed from a second piece of the material and soldered into place to the body (14) (e.g., the base of proximal segment (16) having the proximal hook (18)). Other manufacturing techniques may also be used to increase the performance of the device, to increase the ease of manufacturing, or to otherwise improve the IVC filter (10). In one example of the IVC filter (10), the overall length may be 2⅛" (2.125 inches, 53.98 mm), with the proximal segment (16) length being substantially ⁷⁄₁₆" (0.4375 inch, 11.11 mm), the legs being substantially 1¹¹⁄₁₆" (1.6875 inch, 42.86 mm), the length of the distal segment (20) and distal hook (22) being 1" (1.0 inch, 25.4 mm), the tip-to-tip of the proximal hook (18) to the distal hook (22) being 1⁷⁄₁₆" (1.4375 inch, 36.51 mm), and the maximum width of the IVC filter (10) being substantially 1¾" (1.75 inch, 44.45 mm). Other specifications from those noted herein may also be included, all of which are considered within the scope of the present disclosure.

In a preferred embodiment, the present invention may feature an Inferior Vena Cava (IVC) filter apparatus comprising a rod-shaped body having a fixed length and a plurality of filter legs. In some embodiments, the body may comprise a proximal segment of the body having a fixedly attached proximal hook; and a distal segment of the body having a fixedly attached distal hook. In further embodiments, the distal segment may be fixedly attached to the proximal segment so as to form the continuous rod body with the proximal and distal hooks disposed at opposing ends of the body. In still further embodiments, the plurality of filter legs may be fixedly attached to an outer surface of the body between the proximal and distal segments with the filter legs projecting radially from the outer surface and extending past the distal hook.

In another embodiment, the plurality of filter legs may fold between an expanded position and a collapsed position. In still another embodiment, a total length of the apparatus may be defined by a length of the proximal segment plus a length of the filter legs. In some embodiments, the length of the proximal segment and the total length of the apparatus may have a ratio of less than about 1:5. In other embodiments, the length of the proximal segment and the total length of the apparatus may have a ratio of less than about 1:4, 1:6, 1:7, 1:8, 1:9, or 1:10.

According to one embodiment, the proximal hook and the distal hook may be coaxial and may have a cross-sectional area which is equal to or less than a transverse cross-sectional area of the body. In some embodiments, the transverse cross-sectional area of the body may be less than about 5 mm$^2$. In other embodiments, the transverse cross-sectional area of the body may be less than about 1, 1.5, 2, 2.5, 3, 3.5, 4, 4.5, 5.5, 6, 6.5, 7, 7.5, 8, 8.5, 9, 9.5, or 10 mm$^2$. In some embodiments, the diameter of the body may be less than about 2.5 mm. In other embodiments, the diameter of the body may be less than about 1, 1.5, 2, 3, 3.5, 4, 4.5, 5, 5.5, 6, 6.5, 7, 7.5, 8, 8.5, 9, 9.5, or 10 mm.

In one embodiment, the apparatus may have a total collapsed cross-sectional area of less than about 5 mm$^2$ when the plurality of filter legs are in the collapsed position. In other embodiments, apparatus may have a total collapsed cross-sectional area of less than about 1, 1.5, 2, 2.5, 3, 3.5, 4, 4.5, 5.5, 6, 6.5, 7, 7.5, 8, 8.5, 9, 9.5, or 10 mm$^2$ when the plurality of filter legs are in the collapsed position. In a further embodiment, the apparatus may have a total collapsed diameter of less than about 2.5 mm when the plurality of filter legs are in the collapsed position. In other embodiments, apparatus may have a total collapsed diameter of less than about 1, 1.5, 2, 3, 3.5, 4, 4.5, 5, 5.5, 6, 6.5, 7, 7.5, 8, 8.5, 9, 9.5, or 10 mm when the plurality of filter legs are in the collapsed position.

In some embodiments, the apparatus may have a total expanded cross-sectional area of about 1550 mm$^2$ when the plurality of filter legs are in the expanded position. In other embodiments, the apparatus may have a total expanded cross-sectional area of about 100, 200, 300, 400, 500, 600, 700, 800, 900, 1000, 1100, 1200, 1300, 1400, 1500, 1600, 1700, 1800, 1900 or 2000 mm$^2$ when the plurality of filter legs are in the expanded position. According to some embodiments, the transverse cross-sectional area of the body and the total expanded cross-sectional area may have a ratio of about 1:310. In some other embodiments, the transverse cross-sectional area of the body and the total expanded cross-sectional area may have a ratio of about 1:50, 1:100, 1:200, 1:300, 1:400, 1:500, 1:600, 1:700, 1:800, 1:900, or 1:1000.

In preferred embodiments, the legs and body block only a small percentage of the total expanded cross-sectional area and most of the expanded cross-sectional area is open and does not block the blood flow. In one embodiment, the legs and body may block less than 10 percent of the total expanded cross-sectional area. In other embodiments, the legs and body may block less than 1, 2, 3, 4, 5, 6, 7, 8, 9, 11, 12, 13, 14, 15, 16, 17, 18, 19, 20, 25, 30, 40, or 50 percent of the total expanded cross-sectional area. In some embodiments, the expanded cross-sectional area is about equal to a cross sectional area of an IVC. In some preferred embodiments, the apparatus may block less than 10 percent of an original blood flow through an IVC when it is positioned in the IVC. In other embodiments, the apparatus may block less than 1, 2, 3, 4, 5, 6, 7, 8, 9, 11, 12, 13, 14, 15, 16, 17, 18, 19, 20, 25, 30, 40, or 50 percent of an original blood flow through an IVC when it is positioned in the IVC.

In an embodiment, the length of the proximal segment may be less than about 12 mm. In additional embodiments, the length of the proximal segment may be less than about 1, 2, 3, 4, 5, 6, 7, 8, 9, 10, 11, 13, 14, or 15 mm. Without wishing to limit the invention to a particular theory or mechanism, it is believed that having a proximal segment with a shorter length may provide the proximal hook with a lower potential to imbed into the wall of the IVC if the apparatus tilts. In one embodiment the length of the proximal segment and the total length of the apparatus may have a ratio of less than about 1:5. In other embodiments, the length of the proximal segment and the total length of the apparatus may have a ratio of less than about 1:4, 1:6, 1:7, 1:8, 1:9, or 1:10.

In a further embodiment, the total length of the apparatus may be about 2-8 cm. In still further embodiments, the total length of the apparatus may be about 1-8, 2-3, 2-4, 2-5, 2-6, 2-7, 2-9, or 2-10 cm. In yet another embodiment, the total length of each filter leg may be about 2-8 cm. In still another embodiment, the total length of each filter leg may be about 1-8, 2-3, 2-4, 2-5, 2-6, 2-7, 2-9, or 2-10 cm. According to some embodiments, the plurality of filter legs may comprise three, four, five, six, seven, eight, nine, ten, eleven, twelve or more legs. According to other embodiments, each filter leg may comprise a tine at a distal end.

In another embodiment, the present invention may feature a method of positioning an apparatus in an Inferior Vena Cava (IVC) vein. In an embodiment, the method may comprise: engaging either the proximal hook or the distal hook with a snare having a loop at an end; and pulling the snare to position the apparatus within the vein.

In yet one other embodiment, the present invention may feature a method of removing an apparatus from an Inferior Vena Cava (IVC) vein. As a non-limiting example, the method may comprise: engaging the distal hook with a first snare having a loop at an end; pulling the snare to position the apparatus such that the proximal hook is in an accessible position; engaging the proximal hook with a second snare having a loop at an end; sliding a recovery sheath from the second snare over the apparatus to fold the filter legs to the collapsed position; and pulling on either of the two snares to remove the collapsed apparatus.

In one embodiment, the apparatus may comprise a nitinol material. In other embodiments, the apparatus may comprise a biocompatible material, a plastic, a metal, a polymer, or a base substrate with a biocompatible coating. In a preferred embodiment, the apparatus may be configured to fit within a sheath when the plurality of filter legs are in the expanded position. In another preferred embodiment, the distal hook may allow for repositioning of the apparatus. Without wishing to limit the invention to a particular theory or mechanism, it is believed that the repositioning of the apparatus may allow for easier access of the proximal hook.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An Inferior Vena Cava (IVC) filter apparatus comprising:
   a. a continuous rod-shaped body having a fixed length, the body comprising:
      i. a proximal segment of the body having a fixedly attached proximal hook; and
      ii. a distal segment of the body having a fixedly attached distal hook, the distal segment fixedly attached to the proximal segment so as to form the rod-shaped body with the proximal and distal hooks disposed at opposing ends of the body; and b. a plurality of projections fixedly attached to an outer surface of the body between the proximal and distal segments, each projection comprising a filter leg, said filter legs projecting radially from the outer surface and extending past the distal hook;

wherein the plurality of filter legs fold between an expanded position and a collapsed position, wherein all projections attached to the outer surface of the body between the proximal hook and the distal hook are attached to the body on a same cross-sectional plane;

wherein a total length of the apparatus is defined by a length of the proximal segment plus a length of the filter legs, wherein the length of the proximal segment and the total length of the apparatus have a ratio of less than about 1:5, wherein the proximal hook and the distal hook are coaxial and have a cross-sectional area which is equal to or less than a transverse cross-sectional area of the body, wherein the transverse cross-sectional area of the body is less than about 5 mm.

2. The apparatus of claim 1, wherein the apparatus has a total collapsed cross-sectional area of less than about 5 $mm^2$ when the plurality of filter legs are in the collapsed position.

3. The apparatus of claim 1, wherein the apparatus has a total expanded cross-sectional area of about 1550 $mm^2$ when the plurality of filter legs are in the expanded position.

4. The apparatus of claim 1, wherein the transverse cross-sectional area of the body and a total expanded cross-sectional area have a ratio of about 1:310.

5. The apparatus of claim 1, wherein the length of the proximal segment is less than about 12 mm.

6. The apparatus of claim 1, wherein the total length of the apparatus is about 2-8 cm.

7. The apparatus of claim 1, wherein the total length of each filter leg is about 2-8 cm.

8. The apparatus of claim 1, wherein the apparatus comprises a nitinol material.

9. The apparatus of claim 1, wherein the distal hook allows for repositioning of the apparatus.

10. The apparatus of claim 9, wherein the repositioning of the apparatus allows for easier access of the proximal hook.

11. The apparatus of claim 1, wherein the plurality of filter legs comprises six legs.

12. The apparatus of claim 1, wherein each filter leg comprises a tine at a distal end.

13. A method of positioning the apparatus of claim 1 in an Inferior Vena Cava (IVC) vein, the method comprising:
a. engaging either the proximal hook or the distal hook with a snare having a loop at an end; and
b. pulling the snare to position the apparatus within the vein.

14. An Inferior Vena Cava (IVC) filter apparatus comprising:
a. a continuous rod-shaped body having a fixed length, the body comprising:
i. a proximal segment of the body having a fixedly attached proximal hook; and
ii. a distal segment of the body having a fixedly attached distal hook, the distal segment fixedly attached to the proximal segment so as to form the rod-shaped body with the proximal and distal hooks disposed at opposing ends of the body; and
b. a plurality of projections fixedly attached to an outer surface of the body between the proximal and distal segments, each projection comprising a filter leg, said filter legs projecting radially from the outer surface and extending past the distal hook;

wherein the plurality of filter legs are not configured to slide relative to the body;

wherein the plurality of filter legs fold between an expanded position and a collapsed position, wherein all projections attached to the outer surface of the body between the proximal hook and the distal hook are attached to the body on a same cross-sectional plane;

wherein a total length of the apparatus is defined by a length of the proximal segment plus a length of the filter legs, wherein the length of the proximal segment and the total length of the apparatus have a ratio of less than about 1:5, wherein the proximal hook and the distal hook are coaxial and have a cross-sectional area which is equal to or less than a transverse cross-sectional area of the body, wherein the transverse cross-sectional area of the body is less than about 5 mm.

15. An Inferior Vena Cava (IVC) filter apparatus comprising:
a. a continuous rod-shaped body having a fixed length, the body comprising:
i. a proximal segment of the body having a fixedly attached proximal hook; and
ii. a distal segment of the body having a fixedly attached distal hook, the distal segment fixedly attached to the proximal segment so as to form the rod-shaped body with the proximal and distal hooks disposed at opposing ends of the body; and
b. a plurality of projections fixedly attached to an outer surface of the body between the proximal and distal segments, each projection comprising a filter leg, said filter legs projecting radially from the outer surface and extending past the distal hook;

wherein none of the filter legs extend toward the proximal hook;

wherein the plurality of filter legs fold between an expanded position and a collapsed position, wherein all projections attached to the outer surface of the body between the proximal hook and the distal hook are attached to the body on a same cross-sectional plane;

wherein a total length of the apparatus is defined by a length of the proximal segment plus a length of the filter legs, wherein the length of the proximal segment and the total length of the apparatus have a ratio of less than about 1:5, wherein the proximal hook and the distal hook are coaxial and have a cross-sectional area which is equal to or less than a transverse cross-sectional area of the body, wherein the transverse cross-sectional area of the body is less than about 5 mm.

* * * * *